United States Patent
Matsumura et al.

(10) Patent No.: US 6,342,538 B1
(45) Date of Patent: Jan. 29, 2002

(54) CATALYST FOR THE SYNTHESIS OF METHANOL AND A METHOD FOR THE SYNTHESIS OF METHANOL

(75) Inventors: Yasuyuki Matsumura; Wen-Jie Shen, both of Ikeda (JP)

(73) Assignee: Agency of Industrial Science & Technology, Tokyo (JP)

( * ) Notice: Subject to any disclaimer, the term of this patent is extended or adjusted under 35 U.S.C. 154(b) by 0 days.

(21) Appl. No.: 09/449,915

(22) Filed: Dec. 2, 1999

(30) Foreign Application Priority Data

Dec. 17, 1998 (JP) ............................ 10-378652

(51) Int. Cl.⁷ .............................. C07C 27/00

(52) U.S. Cl. ...................... 518/715; 518/700

(58) Field of Search ................. 518/700, 715

(56) References Cited

PUBLICATIONS

Fan Li, Comparison of reduction temperature effect on Pd/Ceo2 catalyst in carbon oxides hydrogenation, J. Grad. Sch. Fac. Eng., Univ. Tokyo, Ser. B (1996), 43 (4), 451–466, 1996.*

* cited by examiner

Primary Examiner—Sreeni Padmanabhan
Assistant Examiner—J. Parsa
(74) Attorney, Agent, or Firm—Rader, Fishman & Grauer, PLLC

(57) ABSTRACT

An object of the present invention is to offer a catalyst for the hydrogenation which is suitable for the synthesis of methanol from CO and/or $CO_2$ under the condition of low temperature and low pressure. In the said catalyst, Pd having a particle size of 5 nm or less is carried on a cerium type oxide ($CeO_2$) whereby methanol is synthesized by the reaction of CO and/or $CO_2$ with hydrogen. The said catalyst for the hydrogenation can be manufactured by a method where the catalyst is manufactured from a coprecipitate of a precursor of cerium type oxide and palladium and a method where palladium is separated in a cerium type oxide.

13 Claims, No Drawings

CATALYST FOR THE SYNTHESIS OF METHANOL AND A METHOD FOR THE SYNTHESIS OF METHANOL

BACKGROUND OF THE INVENTION

The present invention relates to a catalyst for hydrogenation of carbon monoxide and/or carbon dioxide and also to a method for the synthesis of methanol from carbon monoxide and/or carbon dioxide using the hydrogenating catalyst.

Synthesis of methanol from synthetic gas was industrialized in 1923 in Germany by means of a gas phase reaction process using a zinc-chromium catalyst under the reaction condition of 200 atmospheres and 400° C. In 1959, a copper-zinc catalyst (CuO—ZnO) was developed in England and, in 1966, synthesis of methanol under the condition of reaction pressure of 50 atmospheres was industrialized.

After that, improvements in the copper-zinc catalyst and the reaction process have made a progress and, at present, operation is carried out under the reaction condition of 50–100 atmospheres and not higher than 300° C. Particularly for increasing the methanol concentration at the outlet of the reaction and for making the costs for equipment and operation advantageous, reaction pressure of 80–100 atmospheres is most preferred. However, in order to keep such a high reaction pressure, motive power for increasing the pressure is necessary and there is a problem that the cost therefor is high.

Therefore, in reducing the operation cost, the reaction is to be carried out at lower pressure but, in case the reaction pressure is 20 atmospheres for example, when an operation is carried out using a starting gas consisting of 33% by volume of carbon monoxide and 67% by volume of hydrogen, the equilibrium conversion rate of methanol is only 21% at the reaction temperature of 250° C. and that is not practical while, at the reaction temperature of 200° C., the equilibrium conversion rate is 60% but, since the catalytic activity is not sufficient, quite a large amount of catalyst is necessary and that is not practical as well. Accordingly, in the prior art, it has not been possible to make the reaction pressure lower than 50 atmospheres.

With regard to a catalyst other than the copper-zinc catalyst for the synthesis of methanol, it has been reported that a palladium catalyst prepared by means of an impregnation method using a rare earth metal oxide as a carrier is active for the synthesis of methanol (*Journal of the Chemical Society, Chemical Communications*, 1982, no. 12, page 645). However it has a disadvantage that the reactivity is low and, in addition, it exhibits a low selectivity of methanol because methane is by-produced.

As such, the catalysts for the synthesis of methanol up to now have no sufficient reactivity at the reaction temperature of around 200° C. and, therefore, they are unable to lower the reaction pressure.

SUMMARY OF THE INVENTION

An object of the present invention is to offer a catalyst for hydrogenation of carbon monoxide and/or carbon dioxide having a high activity (especially the activity at low temperature) and particularly having a selectivity to methanol or, in other words, to offer a catalyst for the synthesis of methanol and also to offer a method for the synthesis of methanol having a high reaction efficiency.

The present inventors have carried out various experiments and studies for such an object and have found that, in a catalyst where palladium is carried on a metal oxide type carrier including cerium type oxide, dispersibility (particle size) of palladium affects the activity at low temperature and selectivity as the catalyst for hydrogenation and, when a catalyst having a high dispersibility of palladium is used for hydrogenation of carbon monoxide and/or carbon dioxide, high activity at low temperature and selectivity to methanol are achieved and that a catalyst having a high dispersibility of palladium can be prepared by a specific method, whereupon the present invention has been accomplished.

The present invention offers a catalyst for hydrogenation of carbon monoxide and/or carbon dioxide, a catalyst for the synthesis of methanol, a method for the synthesis of methanol and, a method for the hydrogenation of carbon monoxide and/or carbon dioxide which will be mentioned as follows.

The catalyst for hydrogenation of carbon monoxide and/or carbon dioxide according to the present invention is that where palladium having a particle size of 5 nm or less is carried on a metal oxide type carrier containing cerium type oxide.

The above catalyst for hydrogenation can be prepared as a coprecipitate of a precursor of a metal oxide type carrier containing cerium oxide type oxide (such as a hydroxide containing cerium) with palladium.

The catalyst for hydrogenation can also be prepared by mixing a solution where a metal oxide type carrier containing cerium oxide type oxide is dispersed with a solution of palladium compound and an alkaline solution whereby palladium is separated as a hydroxide. Further, the said catalyst for hydrogenation may be in such a form that, if necessary, the palladium hydroxide is converted to an oxide by heating the said catalyst or that, if furthermore necessary, a reduction treatment is carried out whereby the palladium oxide is converted to palladium metal.

The above-mentioned catalyst for hydrogenation can be used as a catalyst for the synthesis of methanol from carbon monoxide and/or carbon dioxide.

The method for the synthesis of methanol according to the present invention is that carbon monoxide and/or carbon dioxide are/is made to react with hydrogen in the presence of any of the above-mentioned catalysts for hydrogenation.

It is preferred that, usually, the above reaction is carried out in a gas phase preferably under 10–100 atmospheres and preferably at 150–300° C.

DETAILED DESCRIPTION OF THE PREFERRED EMBODIMENTS

Catalyst for Hydrogenation (Catalyst for Synthesis of Methanol)

The catalyst for hydrogenation according to the present invention is a catalyst ($Pd/CeO_2$ type catalyst) where palladium is carried on a metal oxide type carrier containing cerium type oxide and can be used as a catalyst for the hydrogenation of carbon monoxide and/or carbon dioxide and also as a catalyst for the synthesis of methanol.

The metal oxide type carrier includes cerium type oxide, a mixture of two or more cerium type oxides, and a mixture of one or more cerium type oxide(s) and one or more metal oxide(s) other than the cerium type oxide.

The cerium type oxide includes cerium oxide ($CeO_2$) and compounded oxides of cerium and of one or more metal(s) other than cerium. The metal oxide other than cerium type oxide includes an oxide of metal other than cerium and compounded oxides of two or more metals other than cerium.

Examples of the metal other than cerium are titanium, zirconium and iron. Examples of the metal oxide other than the cerium type oxide are $TiO_2$, $ZrO_2$ and $Fe_2O_3$.

In preferred embodiments, 70% by weight or more, particularly 80% by weight or more, or still particularly 90% by weight or more cerium type oxide is included and, as a cerium type oxide, a metal oxide type carrier containing 70% by weight or more, particularly 80% by weight or more, or still particularly 90% by weight or more cerium oxide ($CeO_2$) is used.

The catalyst for hydrogenation according to the present invention includes a catalyst where palladium is carried as palladium metal and a catalyst where palladium is carried as a palladium compound such as oxide or hydroxide. In a catalyst where palladium is carried as a palladium compound, activity as a catalyst for hydrogenation can be improved by converting the palladium compound into palladium metal. For example, when palladium hydroxide is heated at high temperature (such as 300–600° C.), it can be converted to palladium oxide and the palladium oxide can be converted to palladium metal by means of reduction (such as reduction with hydrogen).

The carrying amount of palladium in the catalyst for hydrogenation according to the present invention in terms of Pd to the sum of palladium and the metal oxide type carrier is that examples of the lower limit are 1% by weight or more, preferably 2% by weight or more, more preferably 5% by weight or more and, particularly preferably, 10% by weight or more while examples of the upper limit are 30% by weight or less, preferably 25% by weight or less and, more preferably, 20% by weight or less. When the carrying amount of palladium is too small, there is a tendency that the activity as a catalyst for hydrogenation is apt to be hardly expressed while, when it is too much, dispersibility of palladium lowers whereby the activity as the catalyst for hydrogenation may lower and, as a result, that is generally disadvantageous in economy.

The catalyst for hydrogenation according to the present invention includes a highly dispersed $Pd/CeO_2$ type catalyst, a coprecipitated $Pd/CeO_2$ type catalyst and a separated $Pd/CeO_2$ type catalyst which will be mentioned below.

(1) Highly Dispersed $Pd/CeO_2$ Type Catalyst

The catalyst for hydrogenation according to the present invention includes a $Pd/CeO_2$ catalyst where dispersibility of palladium is high or, to be more specific, a $Pd/CeO_2$ catalyst (highly dispersed $Pd/CeO_2$ catalyst) where the particle size of palladium is 5 nm or less (preferably 4 nm or less and, more preferably, 3 nm or less).

In the highly dispersed $Pd/CeO_2$ type catalyst, activity as a catalyst for hydrogenation (particularly the activity at low temperature) is high and, moreover, selectivity to methanol is high whereby that is suitable as a catalyst for the synthesis of methanol.

On the contrary, in a $Pd/CeO_2$ type catalyst where dispersibility of palladium is low or particularly in the said catalyst where palladium is carried on silica, activity as a catalyst for hydrogenation (particularly the activity at low temperature) and selectivity to methanol are low. Although the reason therefor is ambiguous, it is likely that, in the highly dispersed $Pd/CeO_2$ type catalyst, activity (particularly the activity at low temperature) as a catalyst for hydrogenation is enhanced due to an interaction of the metal oxide type carrier with palladium which is highly dispersed and carried thereon.

With regard to dispersibility of palladium, the smaller the particle size, the better. Accordingly, it can be estimated, for example, from an X-ray diffraction pattern of the $Pd/CeO_2$ type catalyst which is reduced with hydrogen. Palladium which is carried as a palladium compound (such as an oxide) is reduced to palladium metal by means of reduction with hydrogen. To be more specific, reduction with hydrogen is carried out by heating the $Pd/CeO_2$ type catalyst in a hydrogen gas atmosphere at 300° C. for example.

In the $Pd/CeO_2$ type catalyst in which the particle size of palladium is 5 nm or less, a peak having a half band width of 1.6° or more; that in which the particle size of palladium is 4 nm or less, a peak having a half band width of 2.1° or more; and that in which the particle size of palladium is 3 nm or less, a peak having a half band width of 2.8° or more are observed at the area where the angle of X-ray diffraction (2θ) is near 40°. When the particle size is 2 nm or less, no peak is observed. On the other hand, when the particle size of palladium is more than 5 nm, a peak having a half band width of less than 1.6° is observed in the $Pd/CeO_2$ type catalyst.

The highly dispersed $Pd/CeO_2$ type catalyst may, for example, be manufactured by a method where the precursor of the metal oxide type carrier is coprecipitated with palladium (a coprecipitation method) or by a method where palladium is separated in a metal oxide type carrier as a hydroxide (a separation method).

(2) Coprecipitated $Pd/CeO_2$ Type Catalyst

The catalyst for hydrogenation according to the present invention includes a $Pd/CeO_2$ type catalyst (coprecipitated $Pd/CeO_2$ type catalyst), preferably a highly dispersed $Pd/CeO_2$ type catalyst, manufactured by a method where a precursor of a metal oxide type carrier containing cerium type oxide is coprecipitated with palladium (a coprecipitation method).

For example, when the pH of a mixed solution (starting solution) of palladium compound and metal compound containing cerium compound for forming a metal oxide type carrier is adjusted (usually to a higher side), the precursor of the metal oxide type carrier can be coprecipitated with palladium. In that case, the precursor of the metal oxide type carrier is precipitated, for example, as a hydroxide containing cerium while palladium is precipitated as a hydroxide.

With regard to a metal compound containing a cerium compound for forming the metal oxide type carrier, electrolytes such as acetate, nitrate, sulfate and chloride of metal including cerium, particularly a water-soluble metal compound, can be used. Examples of the metal other than cerium are titanium, zirconium and iron.

With regard to the palladium compound, electrolytes such as acetate, nitrate, sulfate and chloride of palladium, particularly a water-soluble palladium compound, may be used.

With regard to the solvent, water may be used for example and, for dissolving the metal compound including cerium compound or the palladium compound, an acidic aqueous solution such as hydrochloric acid, sulfuric acid and nitric acid may be used as well.

The pH of the starting solution may be adjusted by, for example, mixing the starting solution with an alkaline solution. The starting solution and the alkaline solution may be mixed, for example, by adding the alkaline solution to the starting solution or by adding the starting solution to the alkaline solution which is diluted with a solvent.

With regard to the alkaline solution, an aqueous solution of alkaline metal hydroxide such as NaOH and KOH, an aqueous solution of alkaline metal carbonate such as $Na_2CO_3$ and $K_2CO_3$, an aqueous ammonia solution ($NH_4OH$), etc. may be used.

The catalyst for hydrogenation according to the present invention can be prepared by converting the precursor of a metal oxide type carrier to a metal oxide type carrier. For example, when the precursor of a metal oxide type carrier is a hydroxide containing cerium, it is heated at high temperature (such as around 300–600° C.) whereby a metal oxide type carrier containing cerium is prepared. As a result of heating at high temperature, hydroxide of palladium is converted to an oxide. When the palladium oxide is reduced (such as by reducing with hydrogen), it can be converted to palladium metal.

When the carried amount of palladium in the coprecipitated $Pd/CeO_2$ type catalyst in terms of Pd to the sum of palladium and metal oxide type carrier is made, for example, 1–30% by weight, preferably 10–30% by weight or, more preferably, 10–20% by weight, it is now possible to enhance the activity as a catalyst for hydrogenation of carbon monoxide and/or carbon dioxide.

In the coprecipitated $Pd/CeO_2$ type catalyst, there is no decrease in the specific surface area by an increase in the carried amount of palladium when the carried amount of palladium is within a range of not more than 30% by weight and, therefore, activity of the catalyst can be enhanced by increasing the carried amount of palladium. However, palladium is expensive and, accordingly, the carried amount of palladium is usually made 20% by weight or less whereby an economically advantageous catalyst is prepared.

The coprecipitated $Pd/CeO_2$ type catalyst is suitable as a catalyst for the synthesis of methanol since its activity (particularly, the activity at low temperature) as a hydrogenating catalyst is high and its selectivity to methanol is high as well. By the coprecipitation method, it is possible to improve the dispersibility of palladium (to be more specific, to make the particle size of palladium 5 nm or less, rather 4 nm or less or, particularly, 3 nm or less) and to make the specific surface large. Accordingly, the coprecipitated $Pd/CeO_2$ type catalyst exhibits a high activity as a catalyst for hydrogenation.

When the carried amount of palladium is increased in the case of an impregnation method which has been commonly used, large amount of palladium is carried as blocks at the easily sticking part on the surface of the carrier and, therefore, dispersibility of palladium is deteriorated. In a coprecipitation method, palladium can be carried together with the precipitation (coprecipitation) as a hydroxide, etc. during the course of precipitation of a precursor of the metal oxide type carrier (such as hydroxide). Therefore, in the coprecipitated $Pd/CeO_2$ type catalyst, the metal oxide type carrier and palladium are tightly bonded and, in addition, dispersibility of palladium is high.

(3) Separated $Pd/CeO_2$ Type Catalyst

The catalyst for hydrogenation according to the present invention includes a $Pd/CeO_2$ type catalyst (separated $Pd/CeO_2$ type catalyst) or, preferably, a highly dispersible $Pd/CeO_2$ type catalyst manufactured by a method (a separation method) where palladium is separated as a hydroxide in a metal oxide type carrier containing a cerium type oxide.

For example, when pH of a solution (starting solution) of a palladium compound wherein a metal oxide type carrier containing a cerium type oxide is dispersed is adjusted or, usually, adjusted to a higher side, palladium can be separated as a hydroxide.

With regard to a palladium compound, it is possible to use electrolytes such as acetate, nitrate, sulfate or chloride of palladium or, particularly, a water-soluble palladium compound. With regard to a solvent for the starting solution, water may be used for example and, for dissolving the palladium compound, an acidic aqueous solution such as hydrochloric acid, sulfuric acid or nitric acid may be used as well.

The pH of the starting solution may be adjusted by, for example, mixing the starting solution with an alkaline solution. The starting solution and the alkaline solution may be mixed, for example, by adding the alkaline solution to the starting solution or by adding the starting solution to the alkaline solution which is diluted with a solvent.

With regard to the alkaline solution, an aqueous solution of alkaline metal hydroxide such as NaOH and KOH, an aqueous solution of alkaline metal carbonate such as $Na_2CO_3$ and $K_2CO_3$, an aqueous ammonia solution ($NH_4OH$), etc. may be used. When palladium hydroxide is heated at high temperature (such as around 300–600° C.), it can be converted to an oxide and the palladium oxide can be converted to palladium metal by reduction (for example, reduction with hydrogen).

When the carried amount of palladium in the separated $Pd/CeO_2$ type catalyst in terms of Pd to the sum of palladium and metal oxide type carrier is made, for example, 1–30% by weight, preferably 1–20% by weight or, more preferably, 1–10% by weight, it is now possible to enhance the activity as a catalyst for hydrogenation of carbon monoxide and/or carbon dioxide.

In the separated $Pd/CeO_2$ type catalyst, the less the carried amount of palladium, the more the dispersibility of palladium whereby the catalytic activity of palladium per carried amount can be enhanced. However, when the carried amount of palladium is too small such as less than 1% by weight, the total amount of palladium is insufficient and there may be a case where a sufficient activity is not achieved.

The separated $Pd/CeO_2$ type catalyst is suitable as a catalyst for the synthesis of methanol since its activity (particularly, the activity at low temperature) as a hydrogenating catalyst is high and its selectivity to methanol is high as well. By the separation method, palladium is carried by separating on a metal oxide type carrier as a hydroxide and, therefore, it is possible to improve the dispersibility of palladium (to be more specific, to make the particle size of palladium 5 nm or less, rather 4 nm or less or, particularly, 3 nm or less) and to make the specific surface large whereby a separated $Pd/CeO_2$ type catalyst having a high activity as a catalyst for hydrogenation can be prepared.

In a separated $Pd/CeO_2$ type catalyst, palladium is carried on a metal oxide type carrier as a hydroxide and, therefore, it is possible to enhance the dispersibility of palladium. As a result thereof, a catalytic activity of palladium per carried amount can be enhanced and, even when the carried amount of palladium is small, its activity as a hydrogenating catalyst is high.

Mode of Use of Catalyst for Hydrogenation

When the catalyst for hydrogenation according to the present invention is subjected to a reduction with hydrogen prior to use, hydrogenation of carbon monoxide and/or carbon dioxide can be carried out efficiently. As a result of the reduction with hydrogen, palladium which is carried as a palladium compound such as palladium oxide or palladium hydroxide can be made into palladium metal.

There is no particular limitation for the shape of the catalyst for hydrogenation according to the present invention and the catalyst may be used in a form of, for example, powder, granules, fine leaves, pellets, honeycombs, etc.

The catalyst for hydrogenation according to the present invention may be used as a molded catalyst prepared by mixing with known binders which do not affect the reaction such as silica gel followed by molding according to common methods. As a result of use of such a molded catalyst, diffusion of the reaction materials can be promoted and, at the same time, its activity as a catalyst can be appropriately controlled.

Method for Synthesis of Methanol (Hydrogenation Method)

When carbon monoxide and/or carbon dioxide are/is made to react with hydrogen in the presence of the catalyst for hydrogenation according to the present invention, the carbon monoxide and/or carbon dioxide can be hydrogenated whereby methanol can be synthesized.

Reaction of carbon monoxide and/or carbon dioxide can be carried out in a gas phase and, usually, the reaction is carried out by means of a gas phase flow system. To be more specific, a mixed gas (synthetic gas) of carbon monoxide and/or carbon dioxide with hydrogen is contacted with the catalyst for hydrogenation of the present invention whereby the carbon monoxide and/or carbon dioxide can be made to react with hydrogen.

With regard to the mixed gas, any of a mixed gas of carbon monoxide and hydrogen, a mixed gas of carbon dioxide and hydrogen, and a mixed gas of carbon monoxide, carbon dioxide and hydrogen may be used. Although the composition of the mixed gas is not particularly limited, that is usually to be decided by taking the stoichiometric relation of the reaction into consideration.

For example, in the case of a mixed gas of carbon monoxide and hydrogen, the mixed gas wherein the molar ratio of carbon monoxide to hydrogen is 1:2 is to be used in view of the stoichiometric relation of the synthetic reaction of methanol and, usually, it is made 1:1~3 (preferably, 1.5~2.5).

For example, in the case of a mixed gas of carbon dioxide and hydrogen, the mixed gas wherein the molar ratio of carbon dioxide to hydrogen is 1:3 is to be used in view of the stoichiometric relation of the synthetic reaction of methanol and, usually, it is made 1:2~4 (preferably, 2.5~3.5).

For example, in the case of a mixed gas of carbon monoxide, carbon dioxide and hydrogen, the mixed gas wherein the molar ratio of the sum of carbon monoxide and carbon dioxide to hydrogen is 1:2~3 is to be used depending upon the molar ratio of carbon monoxide to carbon dioxide in view of the stoichiometric relation of the synthetic reaction of methanol and, usually, it is made 1:1~4 (preferably, 1.5~3.5).

Inert gas such as nitrogen may be present in the mixed gas but, when gas which is other than carbon monoxide, carbon dioxide and hydrogen is present, loss of energy is resulted when the pressure of the mixed gas is raised to a reaction pressure and, therefore, that is not preferred usually.

The reaction pressure may be made usually around 10–100 atmospheres and, preferably, around 20–50 atmospheres. When the reaction pressure is too low, chemical equilibrium and reaction rate are affected and the yield of methanol tends to decrease.

The reaction temperature may be made usually around 150–300° C. and, preferably, around 180–250° C. When the reaction temperature is too low, the catalytic activity (reaction rate) lowers and the yield of methanol tends to decrease. When the reaction temperature is too high, it is necessary to increase the reaction pressure due to a restriction of chemical equilibrium.

The supplying amount of a mixed gas when the reaction is carried out by a gas phase flow method may be appropriately selected depending upon size and shape of reactor, reaction temperature, reaction pressure, etc. and, usually, it may be made around 500~5,000 ml/hour or, preferably, around 2,000~4,000 ml/hour per gram of the catalyst.

As compared with the known catalysts, the catalyst for hydrogenation according to the present invention has a high catalytic activity, shows a good catalytic activity even at low temperature and exhibits a high selectivity to methanol and, therefore, it is useful as a catalyst for the synthesis of methanol. In accordance with the method of the present invention for the synthesis of methanol, it is now possible to synthesize methanol from carbon monoxide and/or carbon dioxide under a low reaction pressure.

As hereunder, manufacturing examples for the catalyst and examples are described so that the characteristic feature of the present invention will be made far clearer.

EXAMPLE 1

Manufacture of the Catalyst for Hydrogenation (Coprecipitation Method)

To 700 ml of distilled water was added 1 ml of 10N hydrochloric acid and, after that, 1.25 g of palladium chloride ($PdCl_2$) and 10.72 g of cerium nitrate ($Ce(NO_3)_4 \cdot 6H_2O$) were dissolved therein to prepare a starting solution. In the meantime, a 1N aqueous solution of sodium carbonate ($Na_2CO_3$) was prepared which is to be used as an alkaline solution (precipitating reagent). The precipitating reagent (the above-prepared alkaline solution) was added to the above starting solution with stirring so that a coprecipitate was produced. When the starting solution was poured into the diluted alkaline solution, the same coprecipitate was able to be produced as well. A dispersion of the coprecipitate produced as such was stirred for one hour so that the reaction was ripened and, after that, the coprecipitate was recovered, well washed with water, dried and heated in air at 500° C. for five hours.

In the resulting catalyst, palladium was highly dispersed in and carried on cerium oxide ($CeO_3$) and the amount of palladium (Pd) carried thereon was 15% by weight. Particle size of palladium estimated from an X-ray diffraction pattern of the catalyst reduced with hydrogen at 300° C. was 4 nm or less.

Manufacture of Methanol

The catalyst obtained in the above coprecipitation method was charged in a fixed-bed flow reactor, heated together with introduction of hydrogen thereinto (reduction of the catalyst with hydrogen) and a reaction gas consisting of 2 volumes of hydrogen and 1 volume of carbon monoxide was supplied at the pressure of 20 atmospheres, the temperature of 200° C. and the space velocity of 3,600 ml/hr/g. The result was that the yield of methanol by hydrogenation of carbon monoxide based upon carbon atom (C) was 27.4 molar % and the selectivity of methanol was 97.5 molar %. The main by-product was methane. Incidentally, the equilibrium yield of methanol under the above reaction condition is 60 molar %.

Comparative Example 1

Manufacturing test of methanol was carried out using a commercially available copper-zinc (CuO—ZnO) type catalyst for the synthesis of methanol under the same conditions as in Example 1. The result was that the yield of methanol by hydrogenation of carbon monoxide based upon carbon atom (C) was 11.3 molar % and the selectivity of methanol was 100 molar %.

When the Comparative Example 1 and Example 1 are compared, it is apparent that, when the catalyst for hydrogenation according to the present invention is used, the yield of methanol is higher than the case where the commercially available catalyst for the synthesis of methanol is used.

Comparative Example 2

Manufacturing test of methanol was carried out under the same condition as in Example 1 except that a $Pd/CeO_2$ catalyst (impregnated $Pd/CeO_2$ catalyst) containing 3% by weight of palladium prepared by an impregnation method was used and the reaction pressure was 30 atmospheres. The result was that the yield of methanol by hydrogenation of carbon monoxide was 0.9 molar % and the selectivity of methanol was 98.8 molar %. The main by-product was methane. Incidentally, the equilibrium yield of methanol under the above reaction condition is 70 molar %.

When the Example 1 and Comparative Example 2 are compared, it is apparent that, when the catalyst for hydrogenation according to the present invention is used, the yield of methanol is higher than the case where the impregnated $Pd/CeO_2$ catalyst is used irrespective of under the condition where the equilibrium yield is low (low pressure).

EXAMPLE 2
Manufacture of Catalyst for Hydrogenation (Separation Method)

After dissolving 0.26 g of palladium chloride ($PdCl_2$) in 300 ml of distilled water, 5 g of cerium oxide ($CeO_2$) was mixed therewith to prepare a starting solution. The starting solution was mixed with a 1N sodium carbonate solution (alkaline solution) as a precipitating reagent to form a precipitate. After that, stirring for maturing, washing with water and drying processes were carried out and burning was conducted at 500° C. for five hours. The amount of palladium carried on the resulting $Pd/CeO_2$ catalyst was 3% by weight. Particle size of palladium estimated from the X-ray diffraction pattern of the catalyst reduced with hydrogen at 300° C. was 3 nm or less.

Manufacture of Methanol

The catalyst obtained in the above separation method was charged in a fixed-bed flow reactor, heated together with introduction of hydrogen thereinto (reduction of the catalyst with hydrogen) and a reaction gas consisting of 3 volumes of hydrogen and 1 volume of carbon dioxide was supplied at the pressure of 20 atmospheres, the temperature of 250° C. and the space velocity of 3,600 ml/hr/g. The result was that the yield of methanol by hydrogenation of carbon dioxide was 10.0 molar % and the selectivity of methanol was 60.8 molar %. The main by-product was monoxide. Incidentally, the equilibrium yield of methanol under the above reaction condition is 12 molar %.

EXAMPLE 3
Manufacture of Catalyst for Hydrogenation (Coprecipitation Method)

After adding 1 ml of a 10N hydrochloric acid solution to 700 ml of distilled water, 1.25 g of palladium chloride ($PdCl_2$) as a palladium compound, 10.46 g of cerium nitrate ($Ce(NO_3)_4.6H_2O$) as a cerium compound and 0.72 g of ferric nitrate ($Fe(NO_3)_3.9H_2O$) as an iron compound were dissolved therein to prepare a starting solution. In the meanwhile, a 1N aqueous solution of sodium carbonate ($Na_2CO_3$) to be used as a precipitating reagent (alkaline solution) was prepared.

The precipitating reagent was added to the starting solution with stirring to form a coprecipitate. It is also possible to give the same coprecipitate by pouring the starting solution into a diluted alkaline solution. A dispersion of the coprecipitate prepared as such was stirred for one hour and the coprecipitate was recovered, well washed with water, dried and burned in air at 500° C. for five hours.

In the resulting catalyst, palladium was highly dispersed in and carried on a mixture of cerium oxide and ferrous oxide and the amount of palladium (Pd) carried thereon was 15% by weight. Particle size of palladium estimated from an X-ray diffraction pattern of the catalyst reduced with hydrogen at 300° C. was 4 nm or less.

Manufacture of Methanol

The catalyst obtained in the above coprecipitation method was charged in a fixed-bed flow reactor, heated together with introduction of hydrogen thereinto (reduction of the catalyst with hydrogen) and a reaction gas consisting of 1 volume of hydrogen and 1 volume of carbon monoxide was supplied at the pressure of 20 atmospheres, the temperature of 200° C. and the space velocity of 3,600 ml/hr/g. The result was that the yield of methanol by hydrogenation of carbon monoxide based upon carbon atom (C) was 16.6 molar % and the selectivity of methanol was 97.8 molar %. The main by-product was methane.

What is claimed is:

1. A method for the synthesis of methanol, said method comprising the hydrogenation of carbon monoxide and/or carbon dioxide in the presence of a catalyst, said catalyst comprising palladium carried on a metal oxide type carrier including cerium type oxide in which the particle size of palladium is 5 nm or less.

2. A method for the hydrogenation of carbon monoxide and/or carbon dioxide, said method comprising reacting carbon monoxide and/or carbon dioxide with hydrogen in the presence of a catalyst, said catalyst comprising palladium carried on a metal oxide type carrier including cerium type oxide in which the particle size of palladium is 5 nm or less.

3. The method for hydrogenation according to claim 2, said method comprising reacting the carbon monoxide and/or carbon dioxide with hydrogen in a gas phase.

4. The method for hydrogenation according to claim 3, wherein the reaction pressure is 10–100 atmospheres.

5. The method for hydrogenation according to any of claims 2–4 wherein the reaction temperature is 150–300° C.

6. The method for hydrogenation according to claim 2 or 3, said method comprising obtaining the catalyst from a coprecipitate of a precursor of the metal oxide type carrier and palladium.

7. The method for hydrogenation according to claim 6, wherein the precursor of the metal oxide type carrier is a hydroxide including cerium.

8. The method for hydrogenation according to claim 2 or 3, said method comprising obtaining the catalyst by separation of hydroxide of palladium in the metal oxide type carrier.

9. The method for hydrogenation according to claim 8, said method comprising separating the palladium as a hydroxide by mixing a solution of a palladium compound in which the metal oxide type carrier is dispersed with an alkaline solution.

10. The method for hydrogenation according to claim 8, said method comprising converting the hydroxide of palladium to oxide by heating the catalyst.

11. The method for hydrogenation according to claim 10, said method comprising reducing the catalyst so that oxide of palladium is converted to palladium metal.

12. The method for hydrogenation according to claim 9, said method comprising converting the hydroxide of palladium to oxide by heating the catalyst.

13. The method for hydrogenation according to claim 12, said method comprising reducing the catalyst so that oxide of palladium is converted to palladium metal.

* * * * *